United States Patent
Yonggang

(10) Patent No.: US 7,535,556 B2
(45) Date of Patent: May 19, 2009

(54) METHODS AND APPARATUS FOR OPTICAL ANALYSIS OF SAMPLES IN BIOLOGICAL SAMPLE CONTAINERS

(75) Inventor: Jiang Yonggang, Hampshire (GB)

(73) Assignee: Genetix Limited, Hampshire (GB)

( * ) Notice: Subject to any disclaimer, the term of this patent is extended or adjusted under 35 U.S.C. 154(b) by 174 days.

(21) Appl. No.: 11/806,379

(22) Filed: May 31, 2007

(65) Prior Publication Data

US 2008/0297795 A1 Dec. 4, 2008

(51) Int. Cl.
*G01J 3/28* (2006.01)
(52) U.S. Cl. .................. 356/26; 250/201.1; 250/201.2; 250/201.3
(58) Field of Classification Search ............... 356/317, 356/326, 624; 250/201.1–201.4
See application file for complete search history.

(56) References Cited

U.S. PATENT DOCUMENTS

| | | | |
|---|---|---|---|
| 5,663,794 A * | 9/1997 | Ishizuka | 356/499 |
| 6,130,745 A | 10/2000 | Manian et al. | |
| 6,441,894 B1 | 8/2002 | Manian et al. | |
| 6,823,079 B1 | 11/2004 | Winterot et al. | |
| 2006/0164644 A1 | 7/2006 | Jiang | |
| 2006/0166305 A1 | 7/2006 | Jiang et al. | |
| 2007/0009395 A1 | 1/2007 | Jiang | |

OTHER PUBLICATIONS

Micro-Epsilon Product Guide for the OptoNCDT 2400 Confocal Chromatic Displacement Sensor (Micro-Epsilon of Keonigbacher Str. 15 94496 Ortenburg, Germany, 8 pgs.

* cited by examiner

*Primary Examiner*—Kara E Geisel
*Assistant Examiner*—Abdullahi Nur
(74) *Attorney, Agent, or Firm*—Foley & Lardner LLP

(57) ABSTRACT

An apparatus and method for optically analyzing samples in a biological sample container containing samples arranged at different locations on the base of the container. An optical acquisition device is provided comprising a detector and an objective. The position of the upper and lower surfaces of the base at each of the sample locations is determined by a confocal polychromatic displacement sensor. Light is collected from each of the sample locations by adjusting the focal plane to be coincident with, or vertically offset from, the upper surface of the base, as determined from the displacement sensor. This allows for rapid scanning of large numbers of samples in a multi-well plate or other biological sample containers.

30 Claims, 11 Drawing Sheets

METHODS AND APPARATUS FOR OPTICAL ANALYSIS OF SAMPLES IN BIOLOGICAL SAMPLE CONTAINERS

BACKGROUND OF THE INVENTION

The present invention relates to automated methods and apparatus for optically analyzing samples in biological sample containers such as well plates.

Biological samples such as animal cells, in particular mammalian cells, are commonly cultured in biological sample containers such as well plates (sometimes called microtiter plates or microplates), omni trays, Q-trays and Petri dishes. Much of the processing of the samples can be performed automatically using robotic apparatus that can deliver containers to and from various stations at which the samples can be observed and imaged using camera equipment, and transferred to other containers using an array of pins on a movable mechanical head.

FIGS. 1A and 1B schematically illustrate an example biological sample container 1 in the form of a well plate with a plurality of wells 5 in a 4×3 array. More typically a well plate used for automated processes on a robotic platform will have an array of wells, e.g. 6, 24, 96, 384, 1536, 3072 or 6144 etc wells, but may sometimes only have a single well. The spacing between the wells and/or the external dimensions of the plates relevant for handling, typically conform to the standard of the Society for Biomolecular Screening (SBS) adopted by the American National Standards Institute (ANSI) or derivates and extensions thereof used in the industry. The ANSI microplate standards include: SBS-1 2004: Footprint Dimensions; SBS-2 2004: Height Dimensions; SBS-3 2004: Bottom Outside Flange Dimensions; and SBS-4 2004: Well Positions of 96, 384, and 1536 well plates. The contents of these microplate standards are incorporated herein by reference, in particular the relevant dimensions.

For example, according to the SBS-4 standard, a 96 well plate has wells spaced apart in a square grid by 9 mm. The corresponding dimensions for 384 and 1536 well plates according to the SBS-4 standard are 4.5 mm and 2.25 mm respectively. Other well plates can have their well spacing dimension calculated on this basis, even if not explicitly covered by the SBS-4 standard, e.g. 24 well plates can be provided with an 18 mm inter-well spacing as an extrapolation of the ANSI standard.

Further, according to the SBS-1 standard, a well plate should have external dimensions of 127.76 mm (length)× 85.48 mm (width)±certain specified tolerances.

References to standard dimensions in relation to well plates made in this document are thus made with reference to the above true standards defined by ANSI, and also derivates from and extensions of these standards used in the industry, as well as covering new standards that may be defined for well plates in the future.

Referring to FIG. 1A, the biological sample container 1 is a tray-like container having a top surface 2 with a number of wells 5 for accommodating biological or chemical samples. FIG. 1B is a schematic cross section along the line A-A' of FIG. 1A. It can be seen from FIG. 1B that each of the wells 5 comprises a side wall 3 and a base 4. In the present case, the well plate 1 is one suitable for optical imaging so the base 4 of each well 5 is transparent, and optionally the side wall 3 also.

For successful imaging, it is necessary to be able to accurately position the sample in the field of view of an imaging camera, and to focus the camera on the plane of interest. For well plate imaging in automated processes, the focusing of the imaging camera needs to be carried out in an automated way, and autofocus systems are generally used in the art for this purpose.

U.S. Pat. No. 6,130,745 [1] and U.S. Pat. No. 6,441,894 [2] describe a prior art technique for focusing a laser beam used to excite fluorescence in cell colonies cultured in wells in a well plate. It is important to accurately position a tightly focused beam within the cell colony so as to avoid exciting fluorescence in unbound fluorescent markers outside the colony. The method involves focusing the laser beam near the lower surface of the base of a well, and detecting light reflected back. The basic principles of this method are schematically illustrated in FIGS. 2A to 2C. A well 15 contains a solution 18 which may contain sample cells to be imaged (not shown). FIG. 2A illustrates the arrangement at a first time $t=t_1$, FIG. 2B illustrates the arrangement at a second time $t=t_2$, and FIG. 2B illustrates the arrangement at a third time $t=t_3$. In each case, the well 15 comprises a side wall 13 and a base 14. The base has a finite thickness as defined by an upper surface and a lower surface thereof. Referring first to FIG. 2A, a laser is disposed beneath the well 15, and light emitted from the laser is focused by a lens 16 to a focal point 17 near the lower surface of the base 14 of the well 15. Then, from the time $t_1$ to the time $t_3$, the focal point 17 is scanned upwards. The reflected light intensity reaches a maximum when the light is focused on the lower surface. This occurs at around the time $t_2$ as shown in FIG. 2B. Thus, the lower surface of the well base is detected. The focus is then advanced upwards by at least the known thickness of the base so that the sample volume defined by the well is focused. It is noted that the base thickness is known from the specification of the well plate provided by the well plate manufacturer. It is further noted that imaging of well plates from below, as shown in this prior art system, is generally preferred for a number of reasons. First, there is generally better optical access from below, since the side walls do not need to be avoided. Second, it avoids having to image through the solution contained in the well. This is problematic, since the volume of liquid solution varies and thus the height of the upper surface of the liquid. Moreover, the upper surface of the liquid can move and inherently is not flat owing to meniscus effects.

With regard to focusing a camera to image the cells, a standard autofocus system may be adequate. However, for a container requiring many images, such as a well plate comprising 96, 384 or 1536 wells, it can be very time-consuming to refocus the camera for each well. This is particularly problematic if no stains or fluorescent tags are used to highlight the cells; the visual contrast between the cells and their surroundings can be insufficient for the optical feedback in the autofocus system to function efficiently. As an example, under these conditions it can take over an hour to image each well in a 96-well plate by refocusing the camera for every well, which is inconveniently slow for an automated system intended to handle many cell samples. Examples of such systems include the Nikon PFS ("perfect focus" ™) system and the Olympus ZDS ("zero drift" ™) system.

FIG. 3 schematically illustrates another prior art laser-based autofocus system of the type which is used by Molecular Devices Corporation in their automated microscope system sold under the trade name ImageXpress MICRO (™). A laser beam 27 from a laser 26 is directed at a glancing angle towards the transparent base 24 of a sample container 21, and the reflections from both an upper surface 24a and a lower surface 24b of the base 24 are detected by a detector 28. As a result of the laser being directed at the base at a glancing angle, the reflected light from the upper surface 24a will take a path 29b which is parallel to, but offset from, a path 29a taken by the reflected light from the lower surface 24b. The position of each path can be used to provide an indication of the location of the respective surface, and the distance between the two paths can be used to determine the thickness of the base. While this technique may function adequately for a perfectly flat base having perfectly flat upper and lower surfaces, in reality this may not be the case. For example, the biological sample container may be bowed, which will cause the light beams 29a and 29b to be divergent and no longer allow accurate measurement of the base thickness.

FIGS. 4A and 4B schematically illustrate another prior art solution which is described in US20070009395A1 [3]. In this solution, a well plate is held in a specially designed vacuum bed and sucked down so its base is pressed against an optically flat surface, thus ensuring that all wells lie in the same plane and thereby obviating the need to focus on every well prior to imaging. Referring to FIG. 4A, the holder includes a vacuum bed having an optically flat planar surface 36 for receiving a lower surface 34 of a biological sample container 31 and a perimeter seal 32 surrounding the vacuum bed. The seal is dimensioned to receive the lower perimeter edge of a standard well plate 31. The holder includes an exhaust outlet for evacuating the space under the well plate 31 so that the well bases 34 are urged against the optical flat 36, thereby ensuring that the bases of all the wells are coplanar with each other as shown in FIG. 4B. This enables many or all of the samples in a container to be imaged sequentially without the need to refocus an imaging camera for every sample. Instead, the camera can be focused just once on one sample in one region of the container, and the focus retained for imaging the remainder of the container. This significantly speeds up the time needed for handling each container. However, this method is only as accurate as the manufacturing tolerances in the thickness of the material between the base of the well plate and the base of each well.

SUMMARY OF THE INVENTION

The invention provides a method of optically analyzing samples in a biological sample container, comprising the steps of:

providing a biological sample container containing a plurality of samples located at respective sample locations distributed over the biological sample container, each sample location being coincident with, or vertically offset from, a base of the biological sample container, wherein the base is defined by upper and lower surfaces;

providing an optical acquisition device comprising a detector and an objective which collectively define a focal plane for optical acquisition;

measuring the position of at least one of the upper and lower surface of the base at each of the sample locations by focusing a continuum of wavelengths of polychromatic light to a continuum of respective pre-calibrated positions along an axis extending through the base, and by collecting, preferably confocally, and spectrally decomposing those components of the polychromatic light scattered from said axis; and collecting light from each of the sample locations by adjusting the focal plane to be coincident with, or vertically offset from, the upper surface of the base based on the position of the at least one of the upper and lower surface of the base measured at that sample location.

The invention further provides an apparatus for optically analyzing samples in a biological sample container, the biological sample container containing a plurality of samples located at respective sample locations distributed over the biological sample container, each sample location being coincident with, or vertically offset from, a base of the biological sample container, wherein the base is defined by upper and lower surfaces, the apparatus comprising:

a container station in which a biological sample container can be arranged;

an optical acquisition device comprising a detector and an objective arranged to view a biological sample container arranged in the container station from below, the positions of the detector and objective collectively defining a focal plane for optical acquisition;

a focal plane sensor arranged to view a biological sample container arranged in the container station from below and comprising: (i) a polychromatic light source operable to generate polychromatic light over a range of wavelengths; (ii) a focusing arrangement with defined axial chromatism arranged to focus respective wavelengths of the polychromatic light to respective pre-calibrated positions along an axis that extends through where the base of a biological sample container arranged in the container station would be; (iii) a detection unit comprising a spectrometer arranged to spectrally isolate components of said polychromatic light scattered from said optical axis, preferably with the aid of a confocal collection aperture; and (iv) a data processing unit operable to determine the position of at least one of the upper and lower surface of the base from the isolated components of the scattered polychromatic light output by the spectrometer;

a positioning apparatus operable to adjust the focal plane of the optical acquisition device relative to the container station; and a controller operable to control the focal plane sensor, optical acquisition device and positioning apparatus to: (i) determine a desired focal plane for each sample location with reference to the determined position of the at least one of the upper and lower surface of the base at that sample location; and (ii) use the optical acquisition device to collect light from each of the sample locations with the focal plane adjusted to its desired setting.

The predetermined relationship between wavelength and position on the optical axis can be known in advance very accurately by factory calibration, and thus the position of an intersection between the base of the sample container and the optical axis can also be known very accurately by detecting the wavelength of reflected light. In this way, the measured position of the base on the optical axis can be used as a reference for accurately determining a focal plane for imaging samples within the sample container. This method of determining the position of the base of a sample container is particularly suitable because it can be achieved very rapidly compared with conventional autofocus and focused laser methods, in which it is necessary to effectively search for the base of the sample container by varying the focal length of the autofocus mechanism over time until the base of the sample container has been detected. In particular, the present technique is able to simultaneously search all positions along the optical axis by focusing light of different wavelengths along the optical axis and detecting the wavelength of light reflected back from the intersection between the base and the optical axis.

The present technique has been specifically developed for well plates in which case the sample locations are defined, or at least confined to, known positions of wells in a standard well plate. However, other biological sample containers may be used such as omni trays, Q-trays, Petri dishes and the like, and may be useful for imaging individual cells or colonies of cells distributed over a Petri dish or other container type, the coordinates of which have been ascertained by standard imaging, as known from imaging devices used in colony pickers.

The detector may be an imaging camera for obtaining an image of a sample within said biological sample container through said base.

The objective is preferably a lens, such as a single lens, but may be a mirror arrangement, or a lens-mirror combination.

In the apparatus, the controller is operable to determine a desired focal plane for each of a plurality of the sample locations prior to collecting light using the optical acquisition device from those sample locations. The plurality of sample locations could be all the sample locations, or a subset such as one or more rows or columns of wells of a well plate, or a contiguous area of wells.

The controller may instead or also be operable to determine a desired focal plane for a sample location and collect light from that location using the optical acquisition device prior to moving to the next sample location. This might be the preferred alternative in a Petri dish or other container when detecting cell colonies distributed over the dish.

Generally, both the upper and lower surfaces of the base will be detected. However, for some sample positions the upper surface position may not be accurately obtained, since this is generally more difficult to measure than the lower surface position. To take account of this possibility, the controller is preferably operable to take the focal plane for each sample location with reference to the measured upper surface position, if available, and otherwise with reference to the measured lower surface position. An alternative solution to the same problem is for the controller to be operable to take the focal plane for each sample location with reference to a support surface on which the base is in contact offset by a base thickness value computed from the difference between the measured upper and lower surface positions, if available, and otherwise with reference to the support surface. For example, an accurate measurement of the lower surface position can be obtained by flattening the base of the biological sample container against an optical flat according to the disclosure of US20070009395A1 [3].

The detector may be an array detector for imaging the sample location, for example a CCD sensor or multi-channel plate sensor. Alternatively, the detector may not have position resolution and be used, for example, for collecting non-spatially resolved fluorescence from the sample location.

The container station may be adapted to accommodate standard well plates having standard external dimensions, or other standard biological sample containers.

The controller may be operable to control the focal plane sensor, optical acquisition device and positioning apparatus assuming that the biological sample container is a well plate having a standard number of wells distributed in standard positions over the well plate.

The controller may be operable to control the focal plane sensor, optical acquisition device and positioning apparatus assuming that the sample locations are positions of single cells or cell colonies provided by a cell or cell colony imager.

In the context of a well plate, the lower surface corresponds to the external surface of the bottom of a well, whereas the upper surface corresponds to the inner surface of a well. If the intersection between the base of the biological sample container and the optical axis is at the inner surface of the biological sample container, the focal plane position can be set to the inner surface, or to a position within the sample container just above the inner surface of the base, which can be achieved by adding a predetermined offset value to the determined position on the optical axis.

Alternatively, if the intersection between the base of the biological sample container and the optical axis is at the outer surface of the biological sample container, a predetermined offset distance to be added to the position of the outer surface. In this case, a position for the focal plane is selected in dependence on a thickness of the base of the biological sample container.

The thickness of the base of the biological sample container, that is the thickness between the bottom of a well and the bottom of the container itself, may be determined by receiving light reflected from an intersection between the outer surface and the optical axis, and light reflected from an intersection between an inner surface of the base of the biological sample container and the optical axis, determining a position on the optical axis of each of the outer surface and inner surface of the base in dependence on a wavelength of light received from each intersection, and determining a thickness for the base from a difference in position on the optical axis between the upper surface and lower surface of the base. The thickness measurements may be filtered to remove spurious measurements, and averaged to produce a mean thickness value for the base of the container. Alternatively, the thickness of the base may be known in advance from the manufacturer.

Two main modes can be used for conducting the focusing and imaging sequence. In a first mode, the controller aligns the focal plane sensor and the biological sample container so that the focal plane sensor is at a position for imaging a region of the biological sample container, then operates the focal plane sensor to determine a position of a focal plane for imaging at the region of the biological sample container, then aligns the imaging camera and the biological sample container so that the imaging camera is at the position for imaging the region of the biological sample container, and then operates the imaging camera to image a sample within the region of the biological sample container at the focal plane determined by the focal plane sensor.

The controller can image a plurality of different regions of the biological sample container by repeatedly performing the sequence of aligning the focal plane sensor, operating the focal plane sensor, aligning the imaging camera and operating the imaging camera.

Alternatively, the controller may align the focal plane sensor and the biological sample container so that the focal plane sensor is at a position for imaging a region of the biological sample container, and operate the focal plane sensor to determine a focal plane for imaging at the region of the biological sample container. In this case, the controller repeatedly aligns and operates the focal plane sensor with respect to the biological sample container to image a plurality of different regions of the biological sample container, generates a focal plane profile for the plurality of different regions, and operates the imaging camera to image samples within the plurality of different regions of the biological sample container at respective focal planes determined in accordance with the focal plane profile.

According to another aspect of the invention, there is provided a method of acquiring images of samples in a biological sample container, comprising the steps of:

providing a biological sample container having a base which is at least partially optically transparent;

determining a focal length for imaging a sample within said biological sample container through said optically transparent base;

focusing at said determined focal length; and obtaining an image of said sample;

wherein said focusing step comprises focusing a continuum of different wavelengths of light from a polychromatic light source to a continuum of different positions on a focal axis, a relationship between said wavelengths and said positions being predetermined;

receiving light reflected from an intersection between said base of said biological sample container and said focal axis;

detecting a wavelength of said received light;

determining a position on said focal axis corresponding to said detected wavelength in accordance with said predetermined relationship between wavelength and position; and determining said focal plane position in dependence on said determined position on said focal axis.

The holder is generally applicable to biological sample containers, such as omni-trays, Q-trays and Petri dishes. However, it is particularly advantageous where the biological sample container is a well plate, which can hold a great number of samples all of which need to be processed, preferably in an automated manner.

The samples may be cells, in particular animal cells. Moreover, the cells could be individual cells, colonies of cells, cell monolayers or other kinds of cell aggregates. The method can be used for picking valuable or interesting cells or colonies of cells from a cell population. The cells may be 1 to 50 in number in the case of individual cells, or much greater in number in the case of colonies.

The samples may be cells, in particular animal cells. Moreover, the cells could be individual cells, colonies of cells, cell monolayers or other kinds of cell aggregates.

Various other aspects and features of the invention are defined in the claims.

BRIEF DESCRIPTION OF THE DRAWINGS

For a better understanding of the invention and to show how the same may be carried into effect reference is now made by way of example to the accompanying drawings in which.

DETAILED DESCRIPTION

Figure 5:
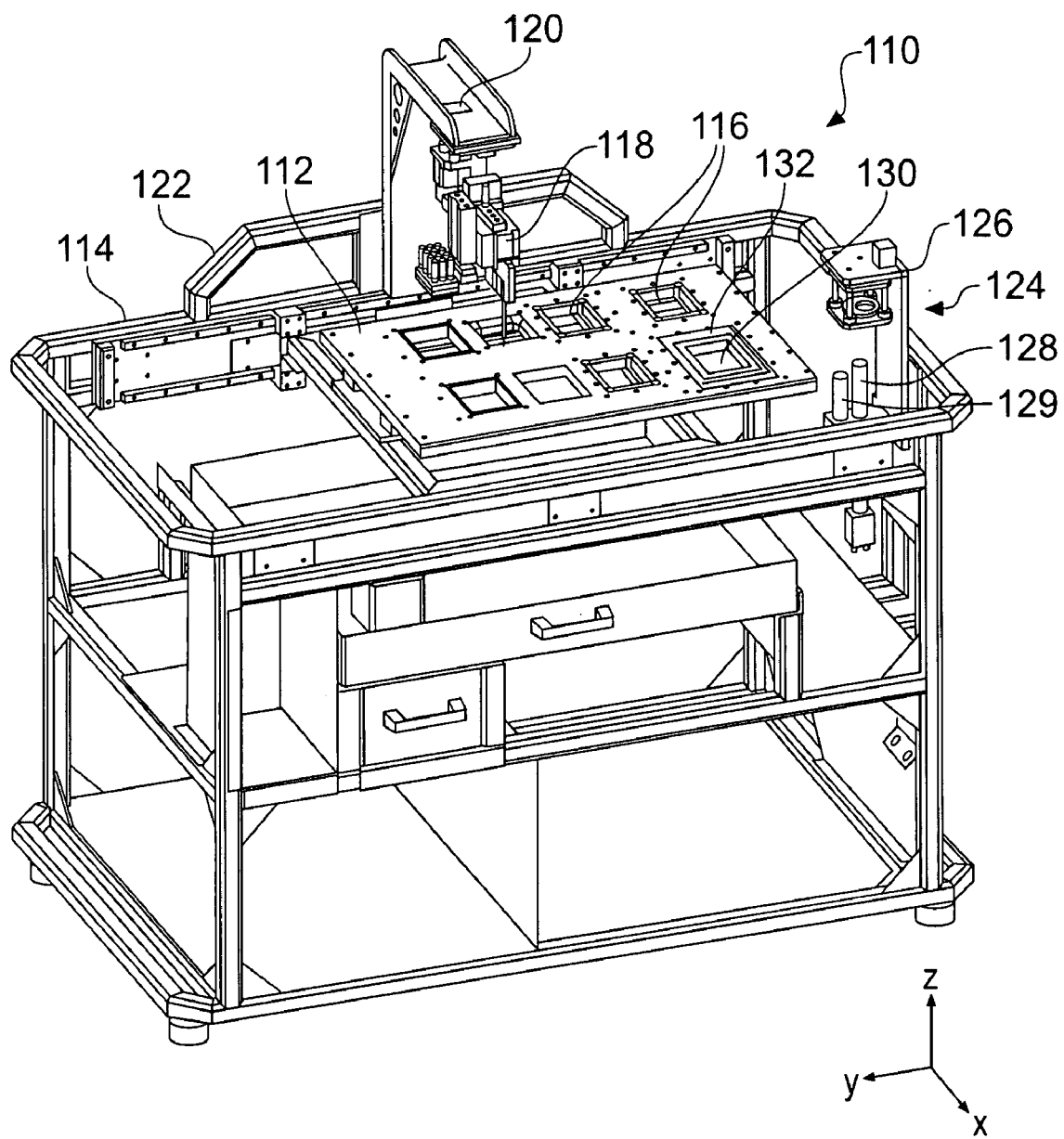
FIG. 5 schematically illustrates an apparatus for handling and processing biological samples in biological sample containers.

FIG. 5 is a perspective view of an apparatus for handling and processing biological samples that embodies aspects of the present invention. However, it is to be understood that the various aspects of the invention may be used with alternative apparatus, containing fewer or more features for handling and processing samples and/or for handling samples in alternative biological sample containers.

The apparatus 110 may be understood as a robot for cell picking having an integrated imaging camera. The apparatus can be subdivided notionally into two-half spaces, one above and one below a main bed 112 which is supported by a frame 114. The main bed 112 is mounted on linear positioners (not shown) so as to be movable relative to the frame 114 in the x and y directions, under the control of a controller (not shown). The controller may be a computer connected by electronic links using standard interface protocols to various automated components of the apparatus 110, with control of the apparatus effected by control software resident in the computer.

A cell picking head 118 is provided that comprises a plurality of hollow pins for aspirating animal cells such as mammalian cells, allowing cells to be picked from one container and deposited in another container. The cell picking head 118 is suspended over the main bed 112 from a gantry 120 by way of a head positioning system made up of x-, y- and z-linear positioners operable to move the cell picking head 118 over the main bed 112. The gantry 120 is mounted on a rail 122 attached to the frame 114 and can slide therealong to give further movement of the cell picking head 118 relative to the main bed 112. All movements can be controlled by the controller.

The main bed 112 contains a plurality of stations 116 (in this case eight) being apertures adapted to receive biological sample containers (not shown) and possibly also components such as a wash/dry station for cleaning the pins after picking. In this example, the apertures are rectangular and shaped to received biological sample containers in the form of well plates, such as plates containing 96, 384 or 1536 wells. However, other containers such as omni trays, Q-trays and Petri dishes may also be handled by providing suitable stations, or using adapters that fit into the well plate stations to hold the containers. The x and y movement of the main bed 112 can be used in conjunction with the movement of the cell picking head 118 to accurately position the pins of the head 118 over particular wells in the well plates. Also, the main bed 112 can be moved to the right hand end of the frame 114 (as illustrated) to bring a container imaging station 130 to an imaging assembly 124 that includes an optical acquisition device.

The imaging assembly 124 is mounted on the frame 114, and comprises a light beam source 126 positioned in the upper half space to direct light downwards onto a well plate held in the container imaging station 130. The optical acquisition part includes a detector in the form of an imaging camera 128 positioned in the lower half space and directed upwards to image cells cultured in the well plate when illuminated by the light source 126, the imaging being through suitable focusing optics, namely an objective (not shown) which may be a single lens or multiple lens combination. Equivalent mirror components could also be used. The imaging assembly also includes a focal plane sensor 129 mounted next to the imaging camera 128. The imaging station 130 includes a holder 132 mounted on the main bed 112 for holding a biological sample container, in this case a well plate.

With the source above the sample and the detector below, a transmission mode optical system is formed. It will be appreciated that a reflection mode optical system may also be used in which the source and detector are both below the sample, or both above. For example, the source and detector optical paths may be combined by a semi-silvered mirror, beam splitter or other known optical components. Reflection mode systems are described in US2006164644A1 [5] and US2006166305A1 [6], the contents of both of which are incorporated herein by reference in their entirety and in particular in respect of the disclosed reflection mode optical configurations on a robotic platform.

Figure 1A:
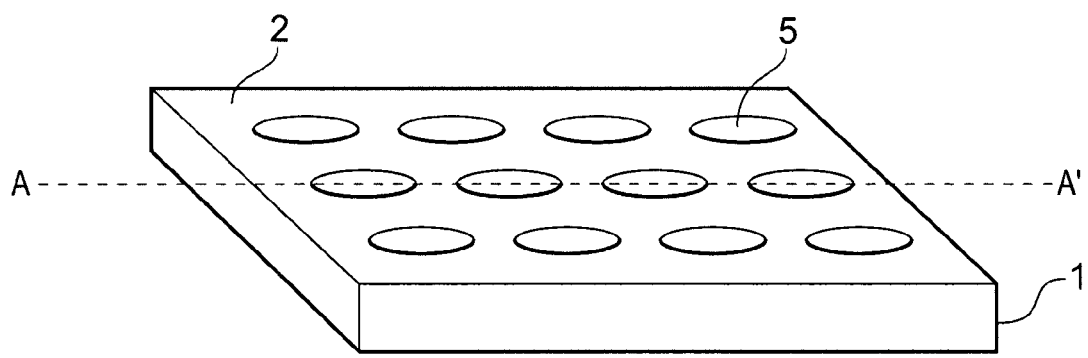
FIGS. 1A and 1B schematically illustrate a standard well plate.
Figure 1B:
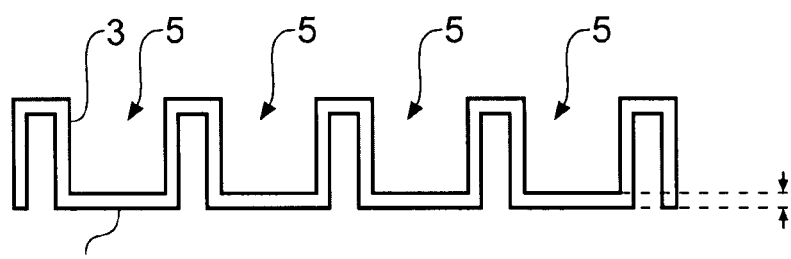
Figures 2A, 2B, 2C:
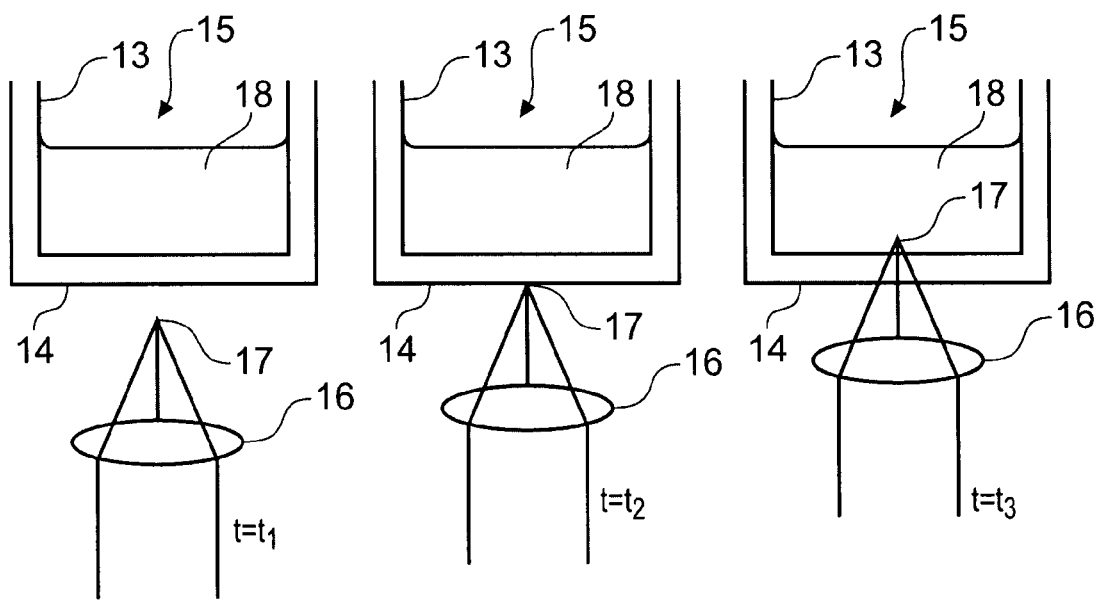
FIGS. 2A to 2C schematically illustrate a prior art laser based focusing method for imaging samples in a biological sample container such as a well plate.
Figure 3:
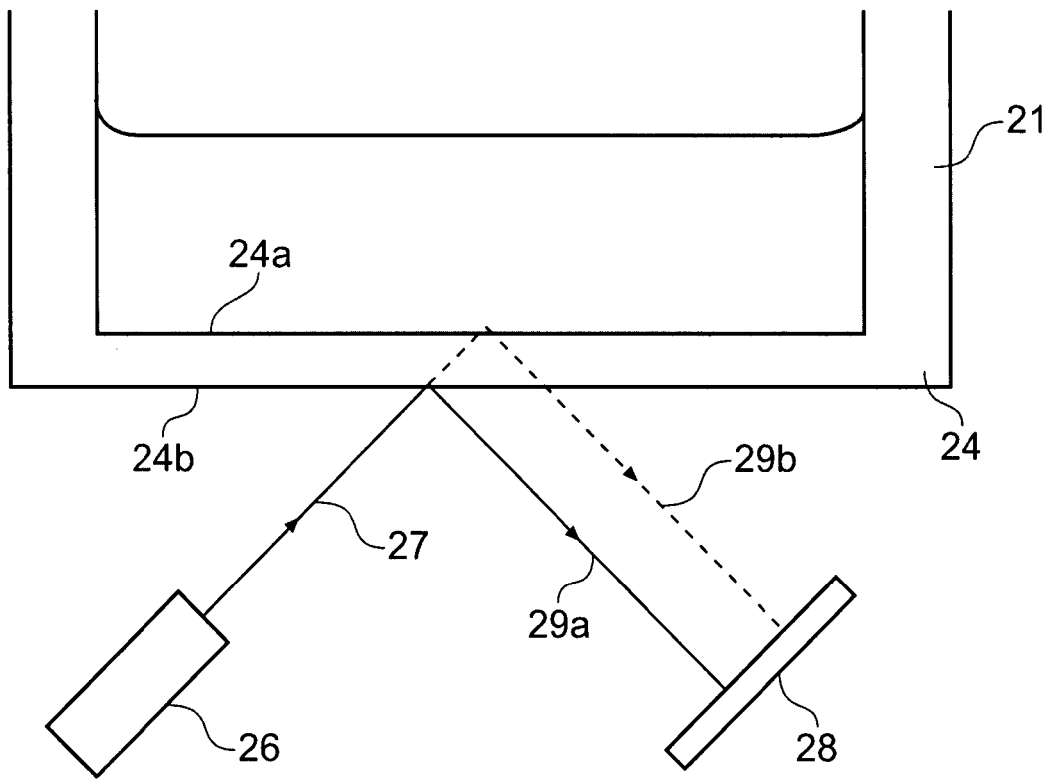
FIG. 3 schematically illustrates another prior art laser based focusing method for imaging samples in a biological sample container such as a well plate.
Figure 6:
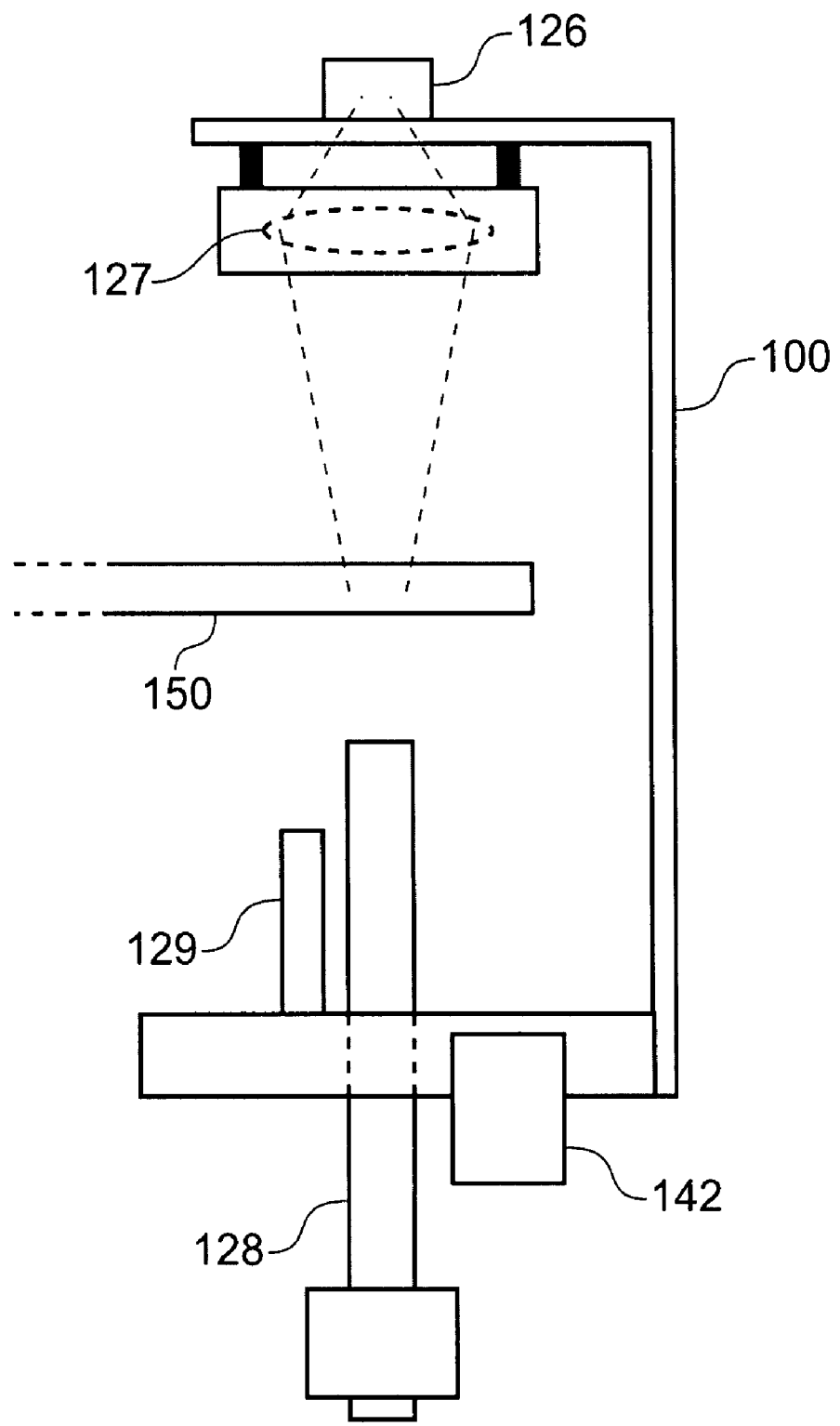
FIG. 6 schematically illustrates an imaging apparatus according to an embodiment of the invention.

FIG. 6 shows a perspective view of the imaging assembly 124 of FIG. 1. The imaging assembly comprises a light beam source 126 mounted at the upper end of a bracket 100 and positioned to direct a beam of illuminating light downwards to an imaging camera 128 mounted at the lower end of the bracket 100. The bracket 100 is configured for mounting of the imaging assembly on the frame 114 of the apparatus 110 so that the beam source 126 is above the main bed 112 and the camera 128 is below the main bed 112 (see FIG. 5). In this way, a biological sample in a well of a well plate 150 held in the imaging station 130 of the main bed 112 can be positioned in the beam path for imaging using the camera. In addition to the camera 128, a focal plane sensor 129 is provided adjacent to the camera which serves to determine a suitable focal plane for the camera 128 to use to image samples in the biological sample container 150.

The light beam source 26 may be an LED (Light Emitting Diode) or one of a variety of other light sources may be used including conventional filament light sources, superfluorescent LEDs, diode lasers, other types of solid state laser or gas lasers. Fixed wavelength or tunable diode lasers may be used. The light source 126 emits light downwards to provide a beam incident on a converging lens 127 supported under the light source. The camera 128 is directed upwards to image samples in a well plate 150 held in the light beam by the main bed 112. The camera 128 includes a DC motor 142 operable to control the focus of the camera in response to focal plane information output from the focal plane sensor 129. The focal plane sensor 129 and the camera 128 are mounted together on the bracket 100 at a known separation. In an alternative embodiment, a focal plane sensor could be provided on a separate bracket and be moveable with respect to the camera.

A controller, which may be a combined controller operable to control all features of the apparatus 110, or a dedicated imaging controller, is connected to the imaging assembly 124. The controller will send the necessary instructions to the various parts of the imaging assembly 124 for obtaining images of samples. Namely, a well of a well plate (or a sample-containing region of a different container) is aligned with the optical axis of the focal plane sensor 129 to determine a focal plane for imaging, and then into the field of view of the camera and into alignment with the beam source 126, using the x and y movement of the main bed 130.

The light source is arranged so that the base of the well is illuminated with a light beam formed by the lens 127, and the camera 128 takes an image of the illuminated well base at the focal plane determined by the focal plane sensor 129. The light source 126 may be switched on and off to provide separate illumination for each image, or may be left on continuously, since the opening of the camera shutter will determine the exposure. In the former case, there is no need to synchronize the illumination with the camera operation. Instead, the camera shutter can be opened for an exposure time that is long compared to a much shorter illumination time, timed to occur during the camera exposure time. Alternatively, the camera shutter can be left open for the duration of the imaging process, and the light source switched on for a brief exposure for each of the well plate positions.

Although the imaging has been described in terms of moving the well plate, it is to be understood that the required relative movements may also be achieved by keeping the well plate stationary and moving the light source and lenses and the camera instead, or by combining movements of these components with movements of the well plate.

Figure 7:
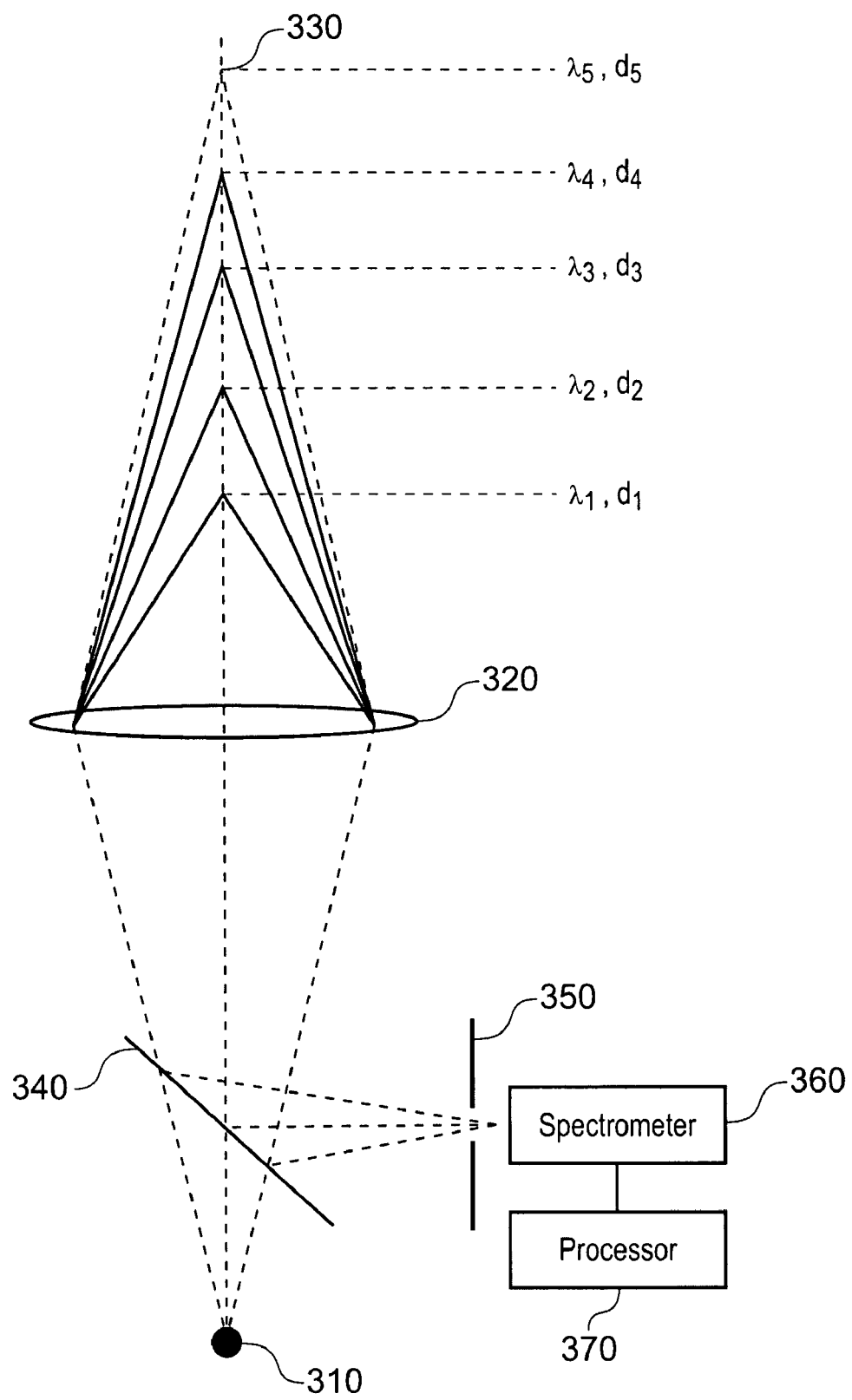
FIG. 7 schematically illustrates a displacement sensor according to an embodiment of the invention.

FIG. 7 schematically illustrates a displacement sensor which can form part of a focal plane sensor. The displacement sensor uses a chromatic confocal optical configuration to detect the relative position of the base of a biological sample container. The relative position of the base of the biological sample container can be used to control an imaging camera to focus at the detected position of the base (or at a selected position relative to the detected position of the base) because the position of the displacement sensor with respect to the imaging camera (and in particular its objective lens) is known. The displacement sensor includes a light source 310 which emits polychromatic light, that is, light having a continuous spread of wavelengths, for example white light. The displacement sensor also includes a lens 320 which focuses the light emitted from the light source 310 at different foci along an optical axis 330 which bisects the lens 320. The lens 320 intentionally exhibits substantial axial chromatism which causes different wavelengths of light to be refracted through the lens by different amounts. In other words, the lens 320 has a refractive index which varies as a function of wavelength. As a result, light emitted from the light source 310 is focused by the lens 320 to provide a continuum of monochromatic focal points distributed along the optical axis 330. In particular, five focal points $d_1$, $d_2$, $d_3$, $d_4$ and $d_5$ are shown in FIG. 7, these being at wavelength $\lambda_1$, wavelength $\lambda_2$, wavelength $\lambda_3$, wavelength $\lambda_4$ and wavelength $\lambda_5$ respectively. Each of these wavelengths is focused to a known position on the optical axis 330, and in particular to a known distance from the lens 320. Specifically, the wavelength $\lambda_1$ corresponds to a distance $d_1$ from the lens 320, the wavelength $\lambda_2$ corresponds to a distance $d_2$ from the lens 320, the wavelength $\lambda_3$ corresponds to a distance $d_3$ from the lens 320, the wavelength $\lambda_4$ corresponds to a distance $d_4$ from the lens 320, and the wavelength $\lambda_5$ corresponds to a distance $d_5$ from the lens 320. It will however be appreciated that the five focal points identified above are not the only points at which light is focused, but rather are example focal points of a continuum of focal points generated along the optical axis 330.

When an object intersects the optical axis 330 at one of the focal points, light striking the object may be scattered back through the lens 320 back towards the light source 310, where it is reflected by a half-silvered mirror 340 towards a detection unit comprising a confocal aperture 350, spectrometer 360 and processor 370. Other forms of beam splitter may be used, as will be understood in the art. Equivalent fiber optic splitter components could also be used.

The light scattered back towards the spectrometer 360 is filtered through the confocal aperture 350 which acts as a spatial filter. The spectrometer 360 detects the intensity and wavelength of the light which it receives, and performs a spectral decomposition of the light scattered from the optical axis to identify the prominent wavelengths. The prominent wavelengths may be those wavelengths at which the intensity of received light exceeds a predetermined threshold. More than one prominent wavelength may occur if an object intersecting the optical axis is at least partially transparent, because such an object would provide at least two relevant intersections, these being the entry and exit points of the optical axis 330 through the object. This property can be used to detect not only the distance of the object from the lens 320, but also the thickness of the object. The prominent wavelengths are then passed to a processor 370 in which is stored a predetermined correspondence between distance relative to the lens 320, or other fixed point along the optical axis, and wavelength. The distances which correspond to each of the prominent wavelengths identified by the spectrometer 360 are then determined. In the context of the arrangement of FIGS. 5 and 6, where the object intersecting the optical axis 330 is the base of a biological sample container, one or more of the distances, which may correspond to a lower surface and an upper surface of the base of the container, can be used to select an appropriate focal plane for imaging of samples in the sample container.

An example of a chromatic confocal device which could be used to implement the displacement sensor is the optoNCDT 2400 Confocal chromatic displacement sensor manufactured by Micro-Epsilon of Koenigbacher Str. 15 94496 Ortenburg, Germany. This device focuses polychromatic white light along an optical axis using a series of lenses which disperse the polychromatic white light into monochromatic light at a given point on the optical axis using the chromatic deviation of the lenses. Each wavelength has a particular distance assigned to it by factory calibration. The light reflected back from a surface intersecting the optical axis is provided to a receiver via a confocal aperture which substantially restricts the light received by the receiver to the light which was precisely focused at the intersecting surface. The receiver then determines the intensity and wavelength of the received light and uses this information to determine the distance from the displacement sensor of an object intersecting its optical axis.

Figure 8:
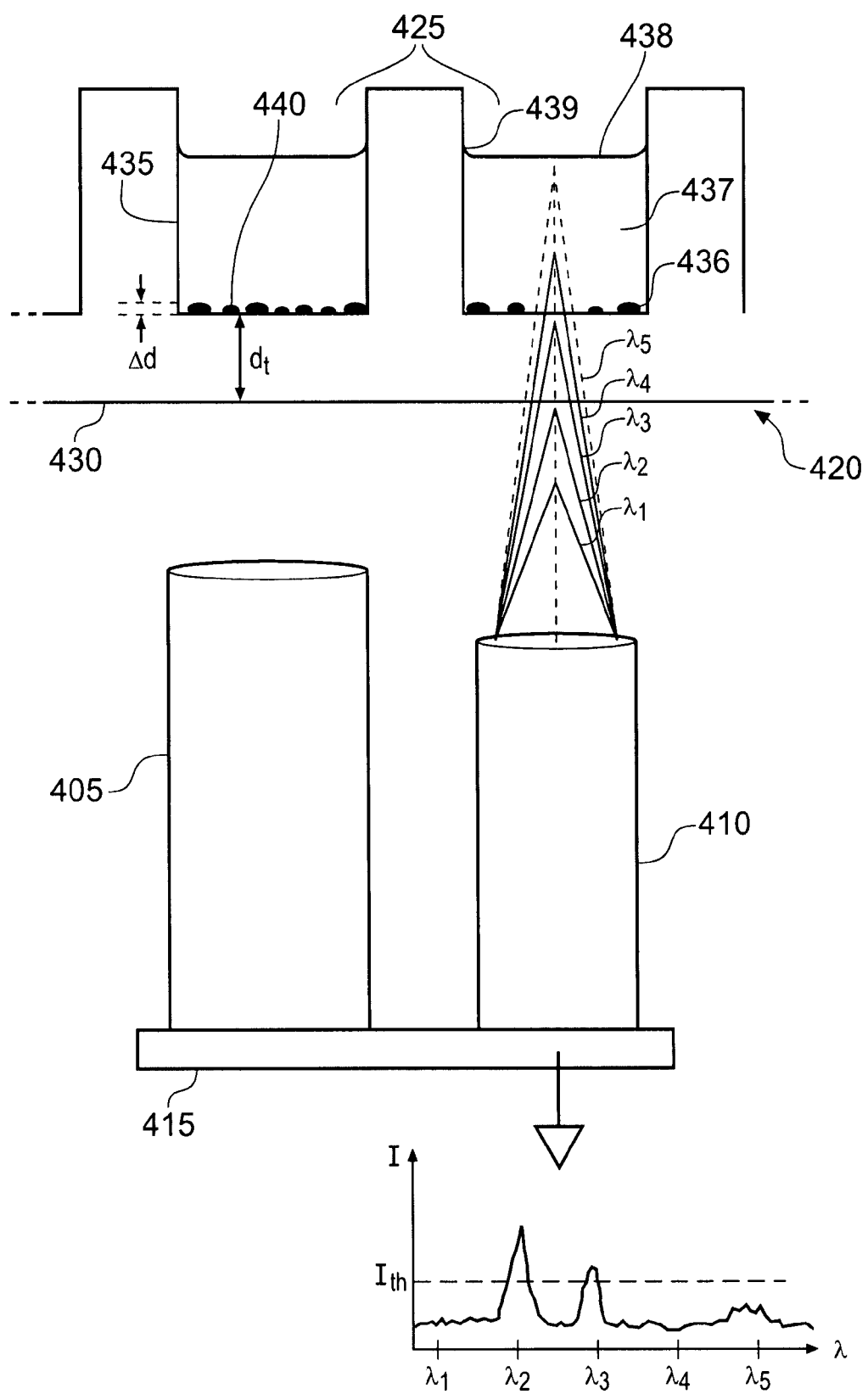
FIG. 8 schematically illustrates the use of a chromatic confocal displacement sensor for detecting the position of a base of a biological sample container according to an embodiment of the invention.

Referring to FIG. 8, a displacement sensor 410, which operates in accordance with the arrangement shown in FIG. 7, is shown in use when determining a suitable focal length for imaging samples in a biological sample container 420. FIG. 8 also shows a camera 405 which is mounted together with the displacement sensor 410 on a mount 415. The camera 405 is relatively positioned with the displacement sensor 410 to provide a one well offset, although it will be appreciated that alternative offsets could be used. In this way, the camera 405 is able to image one well while the displacement sensor 410 detects the focal plane of the next well. As with FIG. 7, the displacement sensor 410 of FIG. 8 generates a continuum of focused points of monochromatic light of different wavelengths along an optical axis, of which five wavelengths are illustrated, these being wavelength $\lambda_1$, wavelength $\lambda_2$, wavelength $\lambda_3$, wavelength $\lambda_4$ and wavelength $\lambda_5$. The biological sample container 420 in this case is a well plate which has a plurality of wells for holding samples. Each well has a wall 435 and a base 440. The wells each contain a solution 437 containing samples 436 to be imaged by the camera 405. The top surface 438 of the solution 437 is also shown, and will generally have a meniscus region adjacent to the side wall, as schematically illustrated. The well to which the displacement sensor 410 is currently being applied has a base portion with a lower surface 430 and an upper surface 440. The base portion has a thickness $d_t$ as measured between the lower surface 430 and the upper surface 440. It can be seen that the focal point of wavelength $\lambda_2$ is intersected by the lower surface 430 of the base of the well, and that the focal point of wavelength $\lambda_3$ is intersected by the upper surface 440 of the base of the well. The focal points of wavelengths $\lambda_1$ and $\lambda_4$ are not intersected in this case by any part of the biological sample container 420. However, the focal point of wavelength $\lambda_5$ intersects with the top surface of the liquid solution 438.

FIG. 8 also shows a schematic example graph of detected light intensity as a function of wavelength, which represents the spectrometer output of the displacement sensor 410 when the biological sample container 420 is at the position shown intersecting the optical axis of the focused light. The horizontal axis of the graph is marked with wavelengths $\lambda_1$, $\lambda_2$, $\lambda_3$, $\lambda_4$ and $\lambda_5$ which correspond to the like-referenced wavelengths of the focal points on the optical axis intersecting the biological sample container. It can be seen from the graph that two intensity peaks arise which exceed a threshold intensity value $I_t$, and that these correspond to wavelengths $\lambda_2$ and $\lambda_3$. These two peaks therefore represent the position of the upper and lower surfaces of the base of the biological sample container 420. All other wavelengths, including $\lambda_1$, $\lambda 4$ and $\lambda_5$, represented on the graph exhibit a level of intensity below the threshold value $I_t$ and are therefore ignored. However, the wavelength $\lambda_5$ exhibits a lower intensity, broader peak due to its interception of the solution top surface 438. By virtue of the known relationship between wavelength and position, the position of the upper and/or lower surfaces of the base of the biological sample container 420 can be determined, and used to set a focal plane for imaging samples in the biological sample container.

The most straightforward method of setting the focal plane is to directly detect the upper surface of the base and use this to set the focal plane, either by setting to focal plane at the upper surface of the base, or by adding a small offset to the upper surface of the base to set the focal plane just above the upper surface within the container itself. This method is most suitable where the position of the upper surface can be determined reliably.

An alternative method of setting the focal plane is available if the upper surface of the base cannot be reliably detected. This may arise when the container is filled with water or a solution, or if some debris exists on the upper surface of the base of the container. In this case, the signal from the upper surface may be either very weak due to the relatively small difference in refractive index between the plastic of the container to the solution held within the container, or unreliable. In order to overcome this problem, the lower surface of the base of the container can be detected, and a thickness value identifying the thickness of the base of the container can be added to the lower surface position to determine the position of the upper surface, and thus the require focal plane position. This method is suitable where the variation in thickness of the base of the container is small, and where the thickness information is available. The lower surface of the base can be detected more easily in this case because of the larger difference in refractive index, n, between the well plate material (e.g. n~1.5-1.6) and air (n=1) compared with the refractive index difference between the well plate material and the liquid contained in the wells (e.g. aqueous solution) which will typically have a refractive index close to that of water (n~1.33).

Known materials for well plates and other biological sample containers include various glasses, such as Pyrex (198), and plastics compounds such as polystyrene (PS), polypropylene (PP), polyethylene (PE), cycloolefin (co-) polymer (COP), styrene-acrylonitrile copolymer (SAN), polyamide (nylon), polyimide (PI), polycarbonate (PC), and polymethyl methacrylate (PMMA).

If the thickness of the base is not known in advance from manufacturers data, it can be derived by detecting both the top and bottom surfaces of the base at a plurality of regions of the sample container, for instance as a scan of the imaging area. The thickness data can be statistically processed to remove data having a large deviation from the mean, and then averaged to obtain a mean value of thickness. This mean value of thickness can be added to the position of the lower surface of the base to identify the position of the upper surface of the base.

Figure 9:
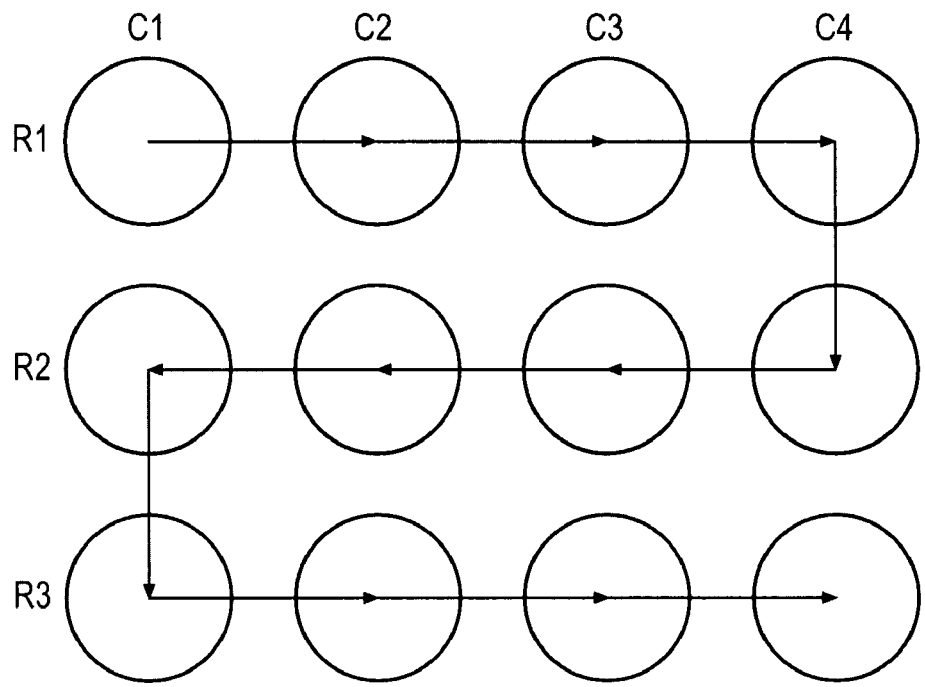
FIG. 9 schematically illustrates a first scanning sequence according to an embodiment of the invention.

FIG. 9 schematically illustrates an example scanning pattern which can be used by both the displacement sensor 410 and the imaging camera 405 when a sequential work flow is used. In the sequential work flow, the displacement sensor scans across all wells in a well plate to identify a suitable focal plane position for each well, with the focal plane information being used to generate a focal plane profile. Then, when a focal plane has been determined for each well, the imaging camera scans across all wells in the well plate, imaging each one in accordance with the respective focal plane position identified in the focal plane profile by suitable adjustment of the camera position with respect of the well. A simple array of twelve wells of a well plate is shown, in 3 rows R1, R2 and R3 and 4 columns C1, C2, C3 and C4. The route of the relative movement between the well plate and the displacement sensor is shown. The scan, both for the displacement sensor and the imaging camera, follows lines in the direction of the arrows. Thus, starting with the upper left well, the wells are focused, and then imaged in the following order: R1C1, R1C2, R1C3, R1C4, R2C4, R2C3, R2C2, R2C1, R3C1, R3C2, R3C3, R3C4 (row wise scanning).

Figure 10:
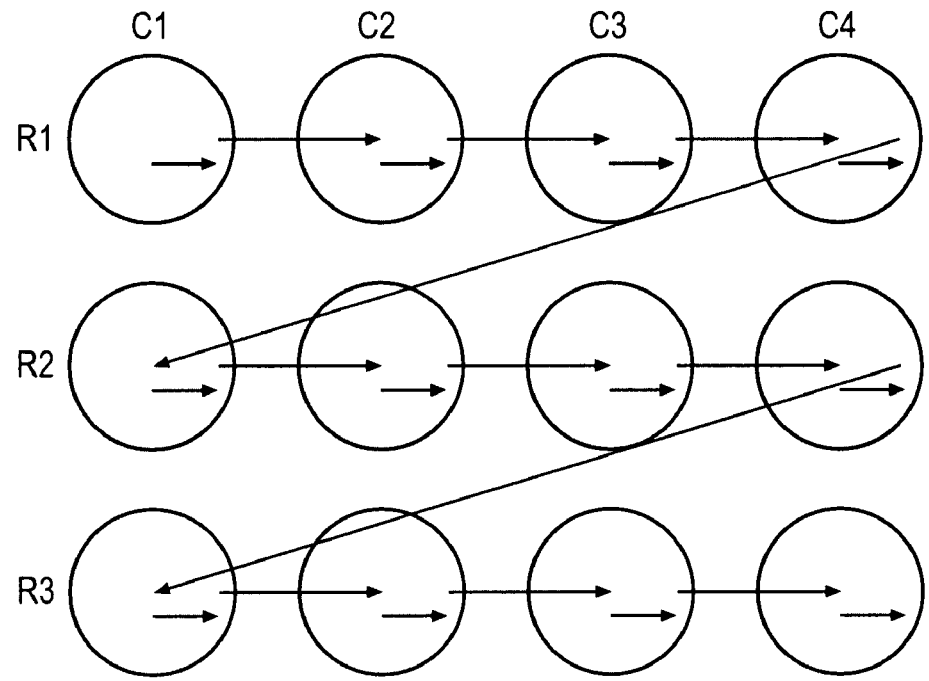
FIG. 10 schematically illustrates a second scanning sequence according to an embodiment of the invention.

FIG. 10 schematically illustrates an example scanning pattern which can be used when an on-the-fly work flow is used. In the on-the-fly method, the displacement sensor and the imaging camera are offset from each other which allows the displacement sensor to be scanned across the areas for imaging slightly ahead of the imaging camera, enabling a focal plane to be selected for imaging based on the detected base position and then used to set the focus of the imaging camera as the camera is brought into the position previously occupied by the displacement sensor.

As with FIG. 9, a simple array of twelve wells of a well plate is shown, in 3 rows R1, R2 and R3 and 4 columns C1, C2, C3 and C4. The route of the relative movement between the well plate and the displacement sensor is shown. The position of the displacement sensor follows lines in the direction of the arrows. Thus, starting with the upper left well R1C1, the displacement sensor determines a focal plane for the well, and then the displacement sensor shifts slightly to the right as indicated by the short arrow to enable the well to be imaged by the offset imaging camera. The displacement sensor then moves to the second well R1C2, where the same process is repeated. In this case, the focusing and imaging order is: R1C1, R1C2, R1C3, R1C4, R2C1, R2C2, R2C3, R2C4, R3C1, R3C2, R3C3, R3C4 (raster scanning with flyback).

Figure 11:
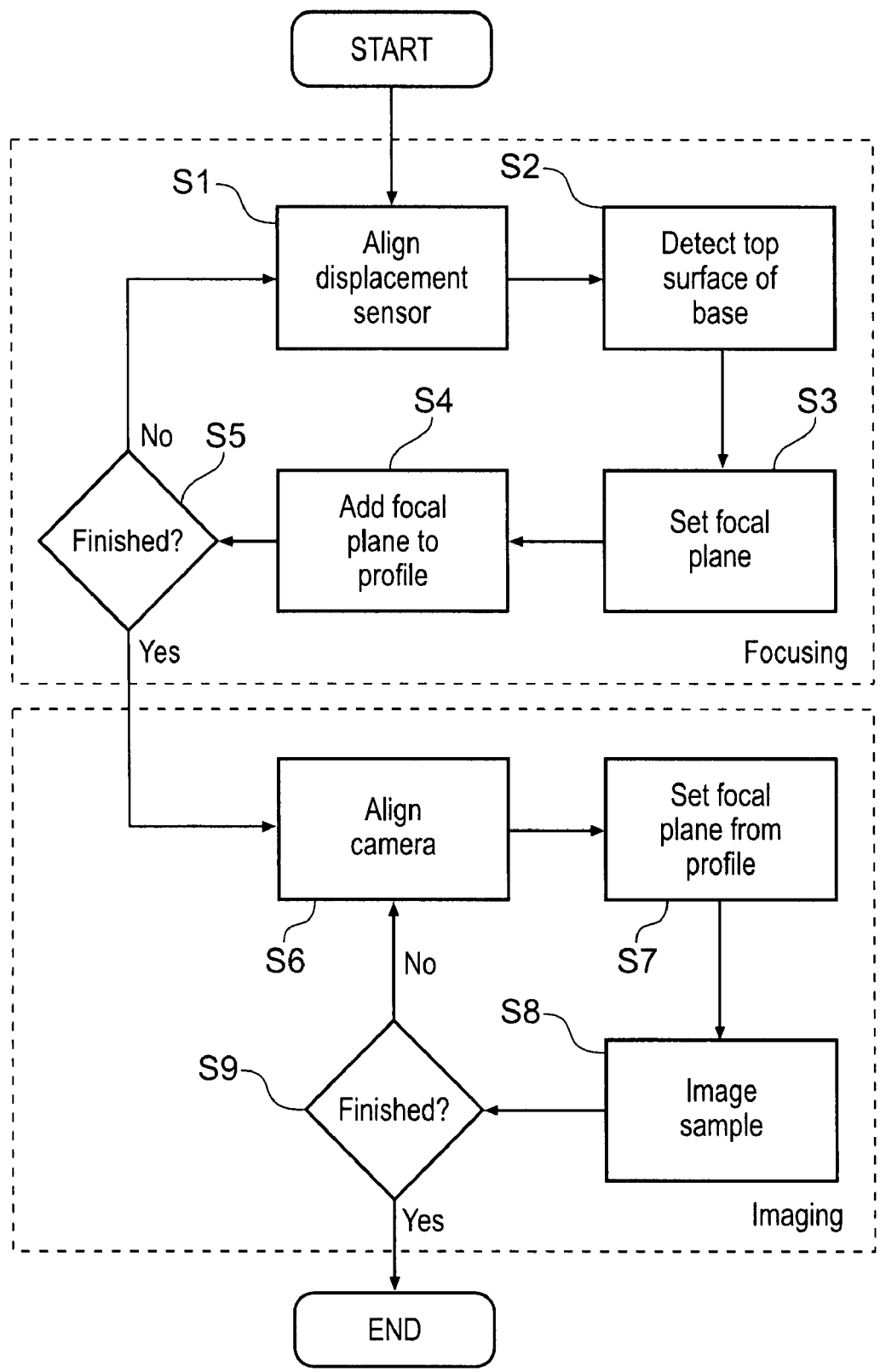
FIG. 11 is a schematic flow diagram which illustrates the first scanning sequence in an embodiment in which the top surface is detected and used to set the focal plane of a well in a well plate.

FIG. 11 schematically illustrates the sequential work flow method in an embodiment where the top surface is detected and used to set the focal plane of a well in a well plate. The process starts at a step S1 in which the displacement sensor is aligned with a well of the well plate. The displacement sensor is then operated at a step S2 to detect and determine the position of the top surface of the base of the well. At a step S3, the determine top surface position is used to set a focal plane position for imaging of the well, and at a step S4 this focal plane position is added to a focal plane profile in association with the well location. At a step S5 it is determined whether the focusing process has finished or whether there are further wells to be focused. If there are further wells to be focused then the process returns to the step S1 where the displacement sensor is brought into alignment with another well of the well plate. If there are no further wells to focus, then the focusing process ends and the imaging process can commence. In particular, at a step S6 the imaging camera is aligned with the first well identified in the focal length profile, and at a step S7 the imaging camera is focused to the focal plane identified in the corresponding entry in the focal plane profile, and then at a step S8 a sample contained in the well is imaged. At a step S9 it is determined whether there are any more wells to image, or whether the imaging process has completed. If there are further wells to image, processing returns to the step S6 where the imaging camera is aligned with another well of the well plate. If there are no further wells to image, then processing terminates.

Figure 12:
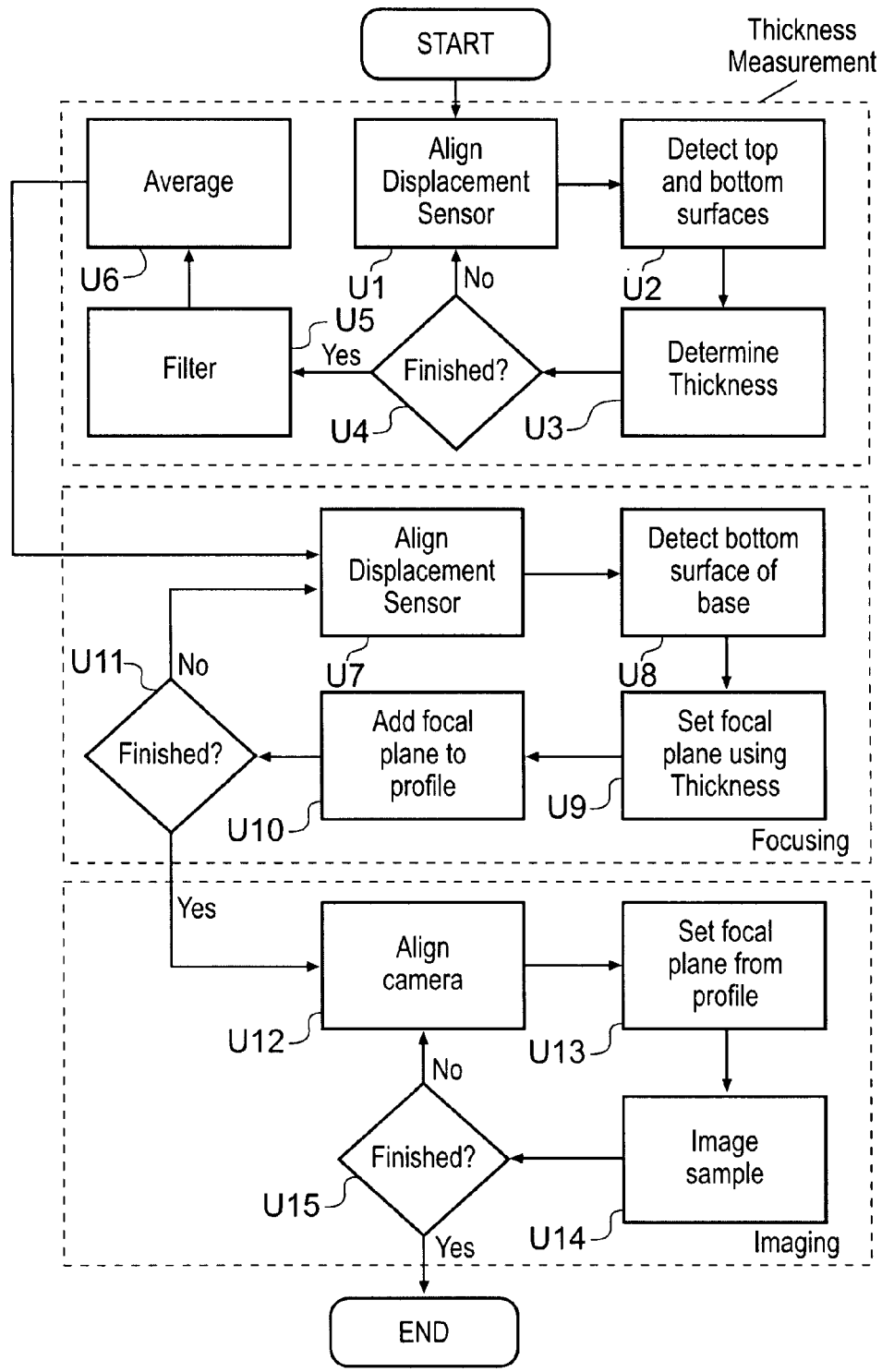
FIG. 12 is a schematic flow diagram which illustrates the first scanning sequence in an embodiment where the bottom surface is detected and used in combination with derived thickness information to set the focal plane of a well in a well plate.

FIG. 12 schematically illustrates the sequential work flow method in an embodiment where the bottom surface is detected and used in combination with derived thickness information to set the focal plane of a well in a well plate. The process can be considered in three stages, the first being a thickness measurement stage, the second being a focusing stage, and the third being an imaging stage. The process starts with a thickness measurement stage and a step U1 in which the displacement sensor is aligned to a well in the well plate. At a step U2 both the upper and lower surfaces of the base of the well are detected and their locations are determined. At a step U3 the separation between the detected upper surface position and lower surface position, which represents the thickness of the base at that point, is determined. At a step U4 it is determined whether any further thickness measurements are to be made, and if so the process returns to the step U1 where the displacement sensor is aligned to another region of the well plate, either at a different point in the same well, or at a different well. If it is determined at the step U4 that no further thickness measurements are to be made, the process moves on to a step U5, where the thickness measurements are filtered to remove measurements which deviate to greatly from the mean thickness measured. This can be achieved by comparing the deviation of each thickness measurement from the mean with a predetermined deviation threshold. Then, the filtered data is averaged at a step U6 to determine an average thickness for the well plate base.

Then, processing moves on to the focusing stage, where the displacement sensor is aligned with a well of the well plate at a step U7. The displacement sensor is then used to determine the position of the bottom surface of the base at a step U8, and the position of the bottom surface is then used to set the position of the focal plane at a step U9 by adding the derived thickness information to the bottom surface position. At a step U10, the focal plane position is added to the focal plane profile. At a step U11 it is determined whether the focusing process has finished or whether there are further wells to be focused. If there are further wells to be focused then the process returns to the step U7 where the displacement sensor is brought into alignment with another well of the well plate. If there are no further wells to focus, then the focusing stage ends and the imaging stage can commence. The imaging stage described by steps U12 to U16 corresponds exactly to the steps S6 to S10 of FIG. 11, and will thus not be described further.

Figure 13:
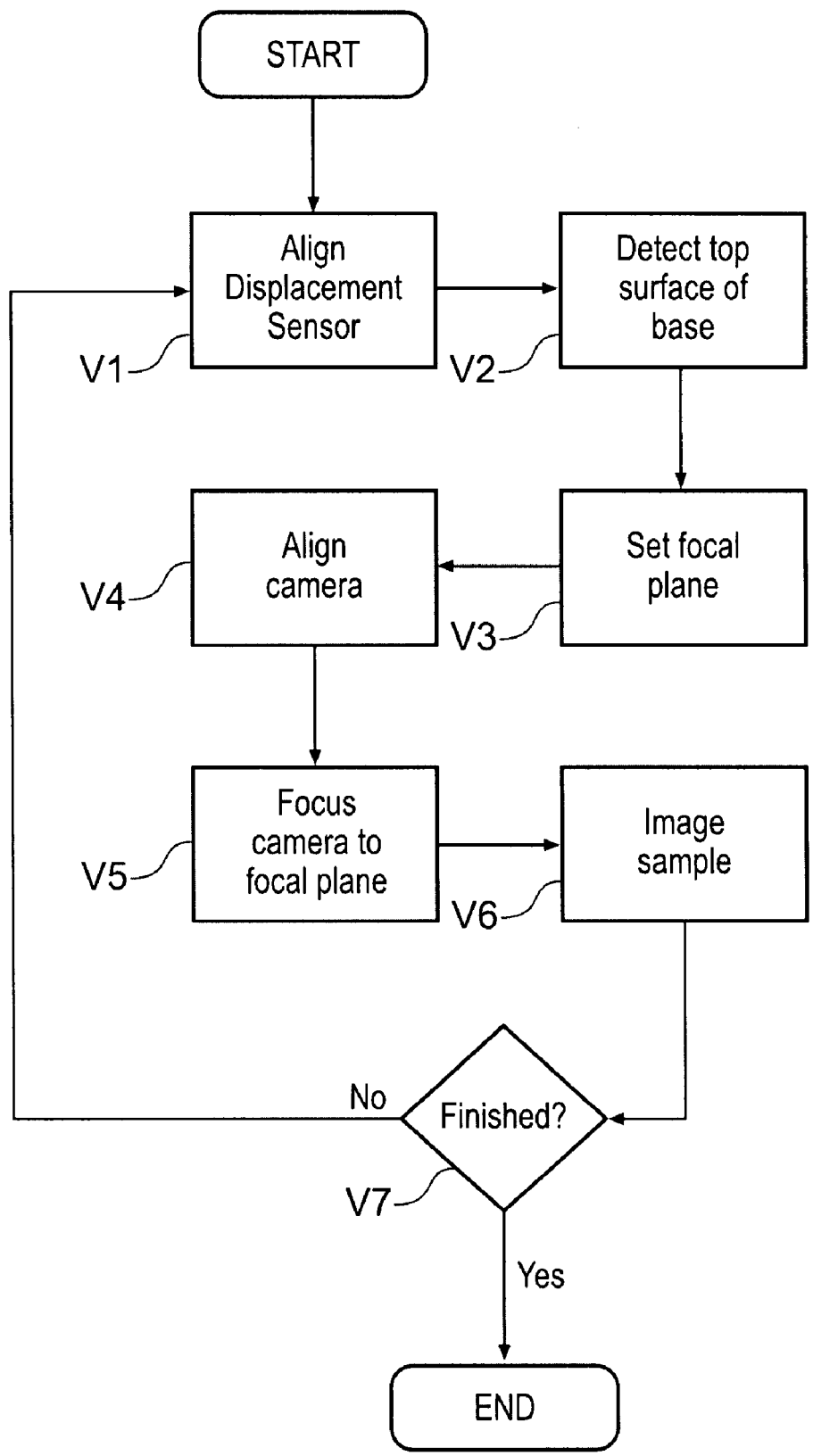
FIG. 13 is a schematic flow diagram which illustrates the second scanning sequence in an embodiment where the top surface is detected and used to set the focal plane of a well in a well plate.

FIG. 13 schematically illustrates the on-the-fly work flow method in an embodiment where the top surface is detected and used to set the focal plane of a well in a well plate. At a step V1 the displacement sensor is aligned with a well of the well plate. The displacement sensor detects the top surface of the base of the well at a step V2 and determines its position. The position of the top surface is used at a step V3 to set a focal plane for the well to be imaged. Then, at a step V4 an imaging camera offset from the displacement sensor is aligned with the well while the imaging camera is focused to the determined focal plane position at a step V5. At a step V6 a sample in the well is imaged at the selected focal plane position. At a step V7 it is determined whether there are any further wells to image, or whether the process has finished. If there are further wells to image, the process returns to the step V1, where the displacement sensor is aligned with a further well. If there are no further wells to image, processing ends.

Figure 14:
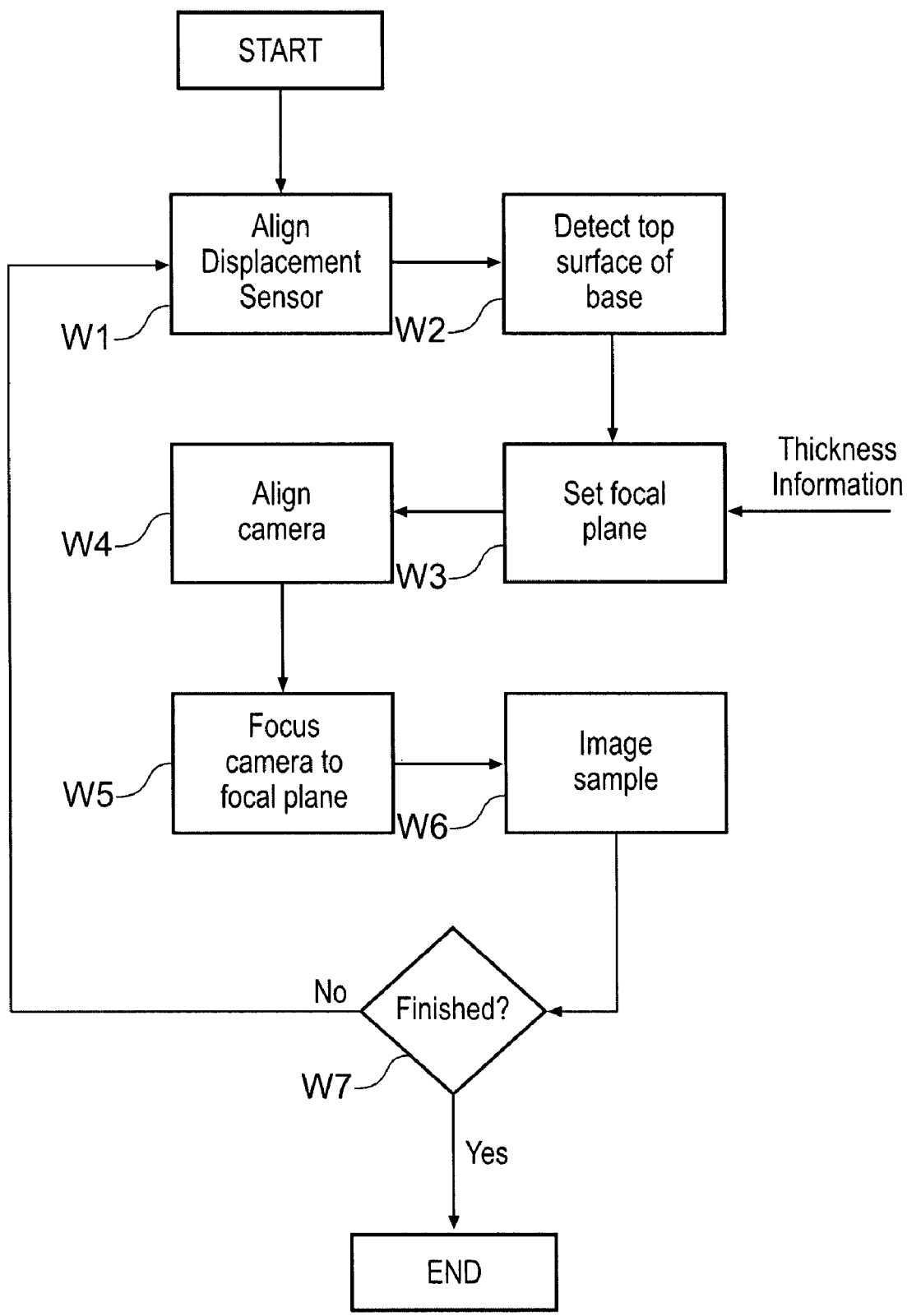
FIG. 14 is a schematic flow diagram which illustrates the second scanning sequence in an embodiment where the bottom surface is detected and used in combination with known thickness information to set the focal plane of a well in a well plate.

FIG. 14 schematically illustrates the on-the-fly work flow method in an embodiment where the bottom surface is detected and used in combination with known thickness information to set the focal plane of a well in a well plate. At a step W1 a displacement sensor is aligned by a well of the well plate. At a step W2 the bottom surface of the base is detected by the displacement sensor and its position determined. The position of the bottom surface is used at a step W3 in combination with known thickness information, for instance provided by the well plate manufacturer, to set a focal plane for the well to be imaged. This can be achieved by adding the thickness of the plate to the determined position of the bottom surface of the well to determine the top surface of the well and thus a suitable focal plane for imaging. Then, at a step W4 an imaging camera offset from the displacement sensor is aligned with the well while the imaging camera is focused to the determined focal plane position at a step W5. At a step W6 a sample in the well is imaged at the selected focal plane position. At a step W7 it is determined whether there are any further wells to image, or whether the process has finished. If there are further wells to image, the process returns to the step W1, where the displacement sensor is aligned with a further well. If there are no further wells to image, processing ends.

For each embodiment of the imaging and scanning described above, the apparatus is preferably controlled by a controller such as a computer, to provide automated handling of biological sample containers.

In the above description, the optical source and detecting camera are mainly described as an illumination and imaging system without reference to spectroscopic properties. However, it will be understood that spectroscopic aspects can be incorporated into the apparatuses and methods of the invention. For example, the imaging may be of fluorescence or Raman properties.

Figure 4A:
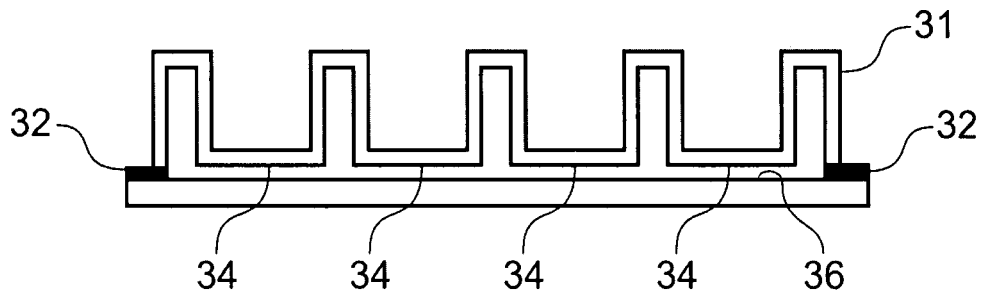
FIGS. 4A and 4B schematically illustrate a further prior art method of aligning samples in a well plate using a vacuum bed with an optical flat.
Figure 4B:
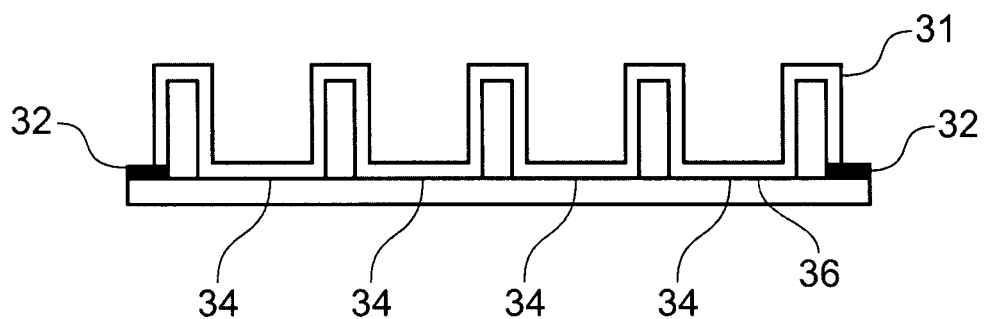

Embodiments of the present invention may work particularly well if combined with the vacuum suction method described with reference to FIGS. 4A and 4B and in US20070009395A1 [3]. In particular, by flattening the base of the biological sample container against an optical flat, it is possible to use the chromatic focal plane sensor of the present invention to measure the thickness of the base of the container in conjunction with the position of the base as defined by the optical flat on which it is held down by vacuum suction. US20070009395A1 [3] is thus incorporated herein by reference in its entirety, in particular its detailed description, associated figures, claims and abstract.

It will be appreciated that although particular embodiments of the invention have been described, many modifications/additions and/or substitutions may be made within the spirit and scope of the present invention.

REFERENCES

[1] U.S. Pat. No. 6,130,745 (Manian et al)
[2] U.S. Pat. No. 6,441,894 (Manian et al)
[3] US20070009395A1 (Genetix Limited)
[4] Micro-Epsilon product guide for the OptoNCDT 2400 Confocal Chromatic Displacement Sensor (Micro-Epsilon of Koenigbacher Str. 15 94496 Ortenburg, Germany)
[5] US2006164644A1 (Genetix Limited)
[6] US2006166305A1 (Genetix Limited)

What is claimed is:

1. An apparatus for optically analyzing samples in a biological sample container, the biological sample container comprising a plurality of samples located at respective sample locations distributed over the biological sample container, each sample location being coincident with, or vertically offset from, a base of the biological sample container, wherein the base is defined by upper and lower surfaces, the apparatus comprising:

a container station in which a biological sample container can be arranged;

an optical acquisition device comprising a detector and an objective arranged to view a biological sample container arranged in the container station from below, the positions of the detector and objective collectively defining a focal plane for optical acquisition;

a focal plane sensor arranged to view a biological sample container arranged in the container station from below and comprising: (i) a polychromatic light source operable to generate polychromatic light over a range of wavelengths; (ii) a focusing arrangement with defined axial chromatism arranged to focus respective wavelengths of the polychromatic light to respective pre-calibrated positions along an axis that extends through where the base of a biological sample container arranged in the container station would be; (iii) a detection unit comprising a spectrometer arranged to spectrally isolate components of said polychromatic light scattered from said optical axis; and (iv) a data processing unit operable to determine the position of at least one of the upper and lower surface of the base from the isolated components of the scattered polychromatic light output by the spectrometer;

a positioning apparatus operable to adjust the focal plane of the optical acquisition device relative to the container station; and a controller operable to control the focal plane sensor, optical acquisition device and positioning apparatus to: (i) determine a desired focal plane for each sample location with reference to the determined position of the at least one of the upper and lower surface of the base at that sample location; and (ii) use the optical acquisition device to collect light from each of the sample locations with the focal plane adjusted to its desired setting.

2. The apparatus of claim 1, wherein the detection unit further comprises a confocal collection aperture arranged to pass light scattered from said optical axis to the spectrometer.

3. The apparatus of claim 1, wherein the controller is operable to determine a desired focal plane for each of a plurality of the sample locations prior to collecting light using the optical acquisition device from those sample locations.

4. The apparatus of claim 1, wherein the controller is operable to determine a desired focal plane for a sample location and collect light from that location using the optical acquisition device prior to moving to the next sample location.

5. The apparatus of claim 1, wherein the controller is operable to take the focal plane for each sample location with reference to the measured upper surface position, if available, and otherwise with reference to the measured lower surface position.

6. The apparatus of claim 1, wherein the controller is operable to take the focal plane for each sample location with reference to a support surface on which the base is in contact offset by a base thickness value computed from the difference between the measured upper and lower surface positions, if available, and otherwise with reference to the support surface.

7. The apparatus of claim 1, wherein the detector is an array detector for imaging the sample location.

8. The apparatus of claim 1, wherein the sample locations are defined by positions of wells in a standard well plate.

9. The apparatus of claim 1, wherein the container station is adapted to accommodate standard well plates having standard external dimensions.

10. The apparatus of claim 1, wherein the controller is operable to control the focal plane sensor, optical acquisition device and positioning apparatus assuming that the biological sample container is a well plate having a standard number of wells distributed in standard positions over the well plate.

11. The apparatus of claim 1, wherein the controller is operable to control the focal plane sensor, optical acquisition device and positioning apparatus assuming that the sample locations are positions of single cells or cell colonies provided by a cell or cell colony imager.

12. A method of optically analyzing samples in a biological sample container, comprising the steps of:
providing a biological sample container containing a plurality of samples located at respective sample locations distributed over the biological sample container, each sample location being coincident with, or vertically offset from, a base of the biological sample container, wherein the base is defined by upper and lower surfaces;
providing an optical acquisition device comprising a detector and an objective which collectively define a focal plane for optical acquisition;
measuring the position of at least one of the upper and lower surface of the base at each of the sample locations by focusing a continuum of wavelengths of polychromatic light to a continuum of respective pre-calibrated positions along an axis extending through the base, and by collecting and spectrally decomposing those components of the polychromatic light scattered from said axis; and
collecting light from each of the sample locations by adjusting the focal plane to be coincident with, or vertically offset from, the upper surface of the base based on the position of the at least one of the upper and lower surface of the base measured at that sample location.

13. The method of claim 12, wherein the components of the polychromatic light scattered from said axis are collected through a confocal aperture to isolate the polychromatic light scattered from said axis.

14. The method of claim 12, wherein the measuring step is carried out for a plurality of the sample locations prior to carrying out the collecting step on those sample locations.

15. The method of claim 12, wherein the measuring and collecting steps are carried out at each sample location prior to moving to the next sample location.

16. The method of claim 12, wherein the focal plane for each sample location is taken with reference to the measured upper surface position, if available, and otherwise with reference to the measured lower surface position.

17. The method of claim 12, wherein the focal plane for each sample location is taken with reference to a support surface on which the base is in contact offset by a base thickness value computed from the difference between the measured upper and lower surface positions, if available, and otherwise with reference to the support surface.

18. The method of claim 12, wherein the detector is an array detector for imaging the sample location.

19. The method of claim 12, wherein the sample locations are wells of a well plate.

20. The method of claim 12, wherein the sample locations are positions of individual cells or cell colonies.

21. The method of claim 12, wherein light is collected from each of the sample locations by moving the sample container from sample location to sample location.

22. The method of claim 12, wherein light is collected from each of the sample locations by moving the optical acquisition device from sample location to sample location.

23. The method of claim 12, wherein the optical acquisition device further comprises a light source.

24. The method of claim 23, wherein the light source is switched on and off to provide illumination for each image at each of the sample locations.

25. The method of claim 23, wherein the optical acquisition device further comprises a camera with a shutter, and wherein light is collected from each of the sample locations by opening the camera shutter to determine the exposure.

26. The apparatus of claim 1, wherein the controller is operable to control the optical acquisition device and positioning apparatus to collect light from each of the sample locations by moving the sample container from sample location to sample location.

27. The apparatus of claim 1, wherein the controller is operable to control the optical acquisition device and positioning apparatus to collect light from each of the sample locations by moving the optical acquisition device from sample location to sample location.

28. The apparatus of claim 1, wherein the optical acquisition device further comprises a light source.

29. The apparatus of claim 28, wherein the controller is operable to switch the light source on and off to provide illumination for each image at each of the sample locations.

30. The apparatus of claim 28, wherein the optical acquisition device further comprises a camera with a shutter, and wherein the controller is operable to control the optical acquisition device to collect light from each of the sample locations by opening the camera shutter to determine the exposure.

* * * * *